United States Patent
Cohen

(10) Patent No.: US 7,184,843 B1
(45) Date of Patent: Feb. 27, 2007

(54) ELECTRODE ARRAY WITH NON-UNIFORM ELECTRODE SPACING

(75) Inventor: Lawrence T. Cohen, Blackburn North (AU)

(73) Assignee: University of Melbourne, Melbourne (AU)

( * ) Notice: Subject to any disclaimer, the term of this patent is extended or adjusted under 35 U.S.C. 154(b) by 0 days.

(21) Appl. No.: 09/649,293

(22) Filed: Aug. 28, 2000

(30) Foreign Application Priority Data

Aug. 27, 1999 (AU) .................................. PQ2498

(51) Int. Cl.
*A61N 1/05* (2006.01)

(52) U.S. Cl. ..................................... 607/137

(58) Field of Classification Search ............ 607/55–57, 607/137
See application file for complete search history.

(56) References Cited

U.S. PATENT DOCUMENTS

| | | | |
|---|---|---|---|
| 4,284,856 A * | 8/1981 | Hochmair et al. .............. 607/9 |
| 4,648,403 A | 3/1987 | Van Compernolle | |
| 5,649,970 A | 7/1997 | Loeb et al. | |
| 6,074,422 A * | 6/2000 | Berrang et al. ............. 607/137 |
| 6,304,787 B1 * | 10/2001 | Kuzma et al. ............... 607/137 |

FOREIGN PATENT DOCUMENTS

| | | | |
|---|---|---|---|
| EP | 0123456 A2 * | 1/2000 | ................. 100/100 |
| WO | WO 96/31087 | 10/1996 | |
| WO | WO 00/71063 A1 | 11/2000 | |

OTHER PUBLICATIONS

Hochmair-Desoyer et al., "An Eight Channel Scala Tymapari Electrode for Auditory Prostheses", IEEE Transactions in Biomedical Engineering, vol. BME-27, No. 1, pp. 44-50 (Jan. 1980).*
Fu and Shannon, "Effects of Electrode . . . Implant", Aug. 1999.*
Fu, et al., "Effects of Electrode Location and Spacing on Phoneme Recognition with the Nucleus-22 Cochlear Implant," *Ear & Hearing*, 1999.
Supplementary European Search Report, May 19, 2004.
International Search Report, PCT/AU00/01020, dated Oct. 9, 2000.

* cited by examiner

*Primary Examiner*—George R. Evanisko
(74) *Attorney, Agent, or Firm*—Jagtiani + Guttag

(57) ABSTRACT

An electrode array for use with a cochlear implant is disclosed, which has electrodes selectively spaced to better target selected regions of the cochlea. In one form, the spacing between adjacent electrodes decreases towards an apical end of the array allowing the electrodes to better target receptors on the inner wall of the scala timpani of the cochlea.

24 Claims, 2 Drawing Sheets

ELECTRODE ARRAY WITH NON-UNIFORM ELECTRODE SPACING

TECHNICAL FIELD

This invention relates to electrode arrays for intra-cochlear implantation.

BACKGROUND ART

Intracochlear electrode arrays have been successfully utilised for many years as a stimulation mechanism for auditory prostheses. The function of the array is to provide electrical stimuli, by selecting one or more electrodes in the array and delivering a stimulus pulse to the electrodes, so as to produce an auditory percept in a patient.

The array is connected to a receiver-stimulator unit, which in turn typically communicates transcutaneously with an externally worn speech processor and sound transducer.

Over time, many different strategies have been applied both to analyse the speech and sound signals received by the transducer, and to provide appropriate stimuli to selected electrodes in the array so as to optimise the speech and sound perception of the patient.

All commercially available cochlear implants utilise electrode arrays in which the electrodes are substantially equally spaced along the length of the array.

Recently, due to an increased understanding of the physiology of the cochlear, a number of proposals have been made to provide and electrode array which is shaped so as to be located near the inner wall of the scala tympani. By position the array in such a location the electrical stimulation delivered by the electrodes to a particular site on the cochlea is more localised resulting in an improved system providing greater auditory perception to the patient.

It is an object of the present invention to provide an electrode array which improves the fidelity of the reproduction of the audio spectrum in the percept of the cochlear implant recipient, for a given number of electrodes.

SUMMARY OF THE INVENTION

Broadly, the present invention provides an electrode array in which the electrodes are not evenly spaced, but rather are differentially spaced in order to better target selected regions of the cochlea.

According to one aspect, the present invention provides an intracochlear electrode array in which the electrodes are closer together at the apical end of the array. This may be achieved in various ways—for example, by a uniformly graduated change in spacing, or by selecting two or more regions of the electrode array to have different spacings.

This aspect of the invention is based on several factors. It has been determined that it is desirable for the spacing of electrodes to correspond to uniform intervals along the organ of Corti. While audio stimulation receptors on the outer wall of the scala tympani are generally regularly spaced, receptors on the inner wall tend to be spaced closer together the further one travels inwardly. It has been determined that receptors on the inner wall of the scala timpani are more sensitive than those on the outer wall, and it would therefore be more effective to stimulate these inner receptors rather than the outer ones as is traditionally done. Preferably, the electrode spacing should be determined by the intercepts, along the intended array placement, of lines passing from a modiolar centre point through points spaced at equal increments along the organ of Corti. This arrangement generally maximises the uniformity of spectral coverage for a given number of electrodes, and accordingly the probability of good speech perception by an implant recipient.

According to another aspect, the present invention provides an electrode array with the spacing of electrodes varied so as to provide a higher density of electrodes at specific regions—for example, along a part of the array intended to stimulate one or more regions of the neural structures corresponding to frequency bands which are considered particularly important for speech recognition. This could be based on many different considerations—the essence of this aspect of the invention is simply to provide electrodes at reduced spacing in areas of particular interest.

BRIEF DESCRIPTION OF THE DRAWINGS

The invention will now be described with reference to the accompanying figures, in which:

Referring to FIG. 1, this is based upon an X-Ray of an implanted device having a curved configuration, for example an array according to PCT/AU99/00391 by Cochlear Limited. It will be appreciated that this is a sectional view showing the scala tympani 10, which in fact curves into the page, but for present purposes the invention can be explained with reference to a two dimensioned projection.

Figure 1:
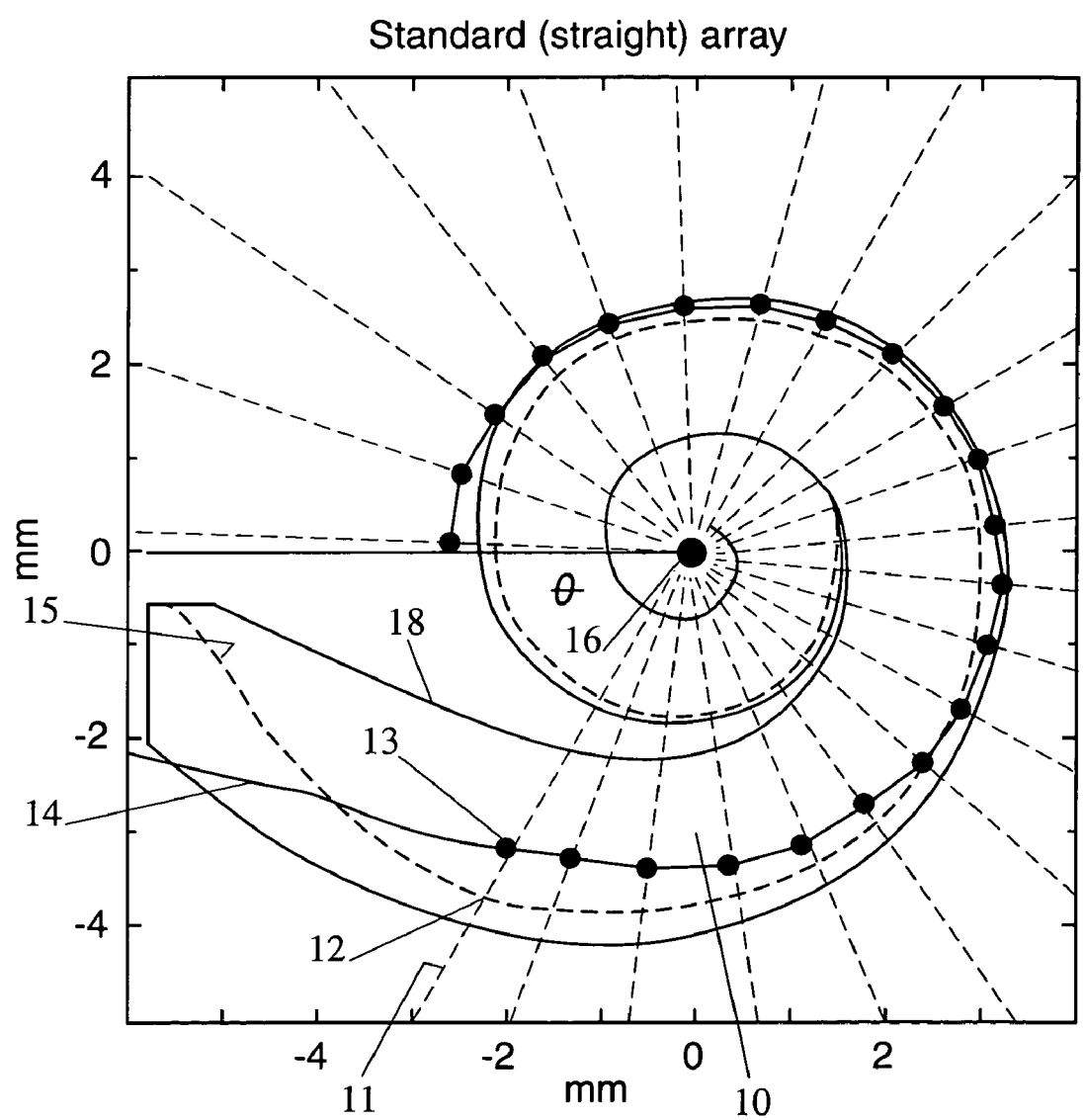
FIG. 1 is a schematic illustration of a conventional electrode array in a scala tympani.

Dotted line 15 represents the organ of Corti, on which the audio receptors 12 are disposed at the intersection of radial lines 11 (only one thus labeled) and the organ of Corti 15. Radial lines 11 are shown extending from the modiolar centre 16, and are of course, purely represented for the purpose of illustrating the present inventive concept. Receptors 12 are composed of neural structures, including spiral ganglion cells, which extend radially inward from the organ of Corti 15. It is in fact these cells which are stimulated by the stimuli produced by electrodes in a cochlear implant.

It will be noted that receptors 12 are disposed at equal intervals along the organ of Corti 15 (at critical bands), even as the curvature increases as the cochlea spirals inwards. The most effective stimulation of these receptors is achieved by direct stimulation by electrodes, and so cochlear implants have been traditionally constructed with electrodes spaced equally to correspond with the spacing of these critical bands. These electrodes are shown as elements 13 on cochlear implant 14.

It has been determined that receptors are more sensitive on the inner wall 18 of the scala timpani 10. Accordingly, it has been found that a better result is achieved by a cochlear implant having electrodes stimulating receptors on the inner wall. To achieve this, the electrodes are caused to lie against the inner wall 18, to make contact with receptors 17 (lying on the intersection of radial lines 11 and the inner wall 18 of scala timpani 10).

Figure 2:
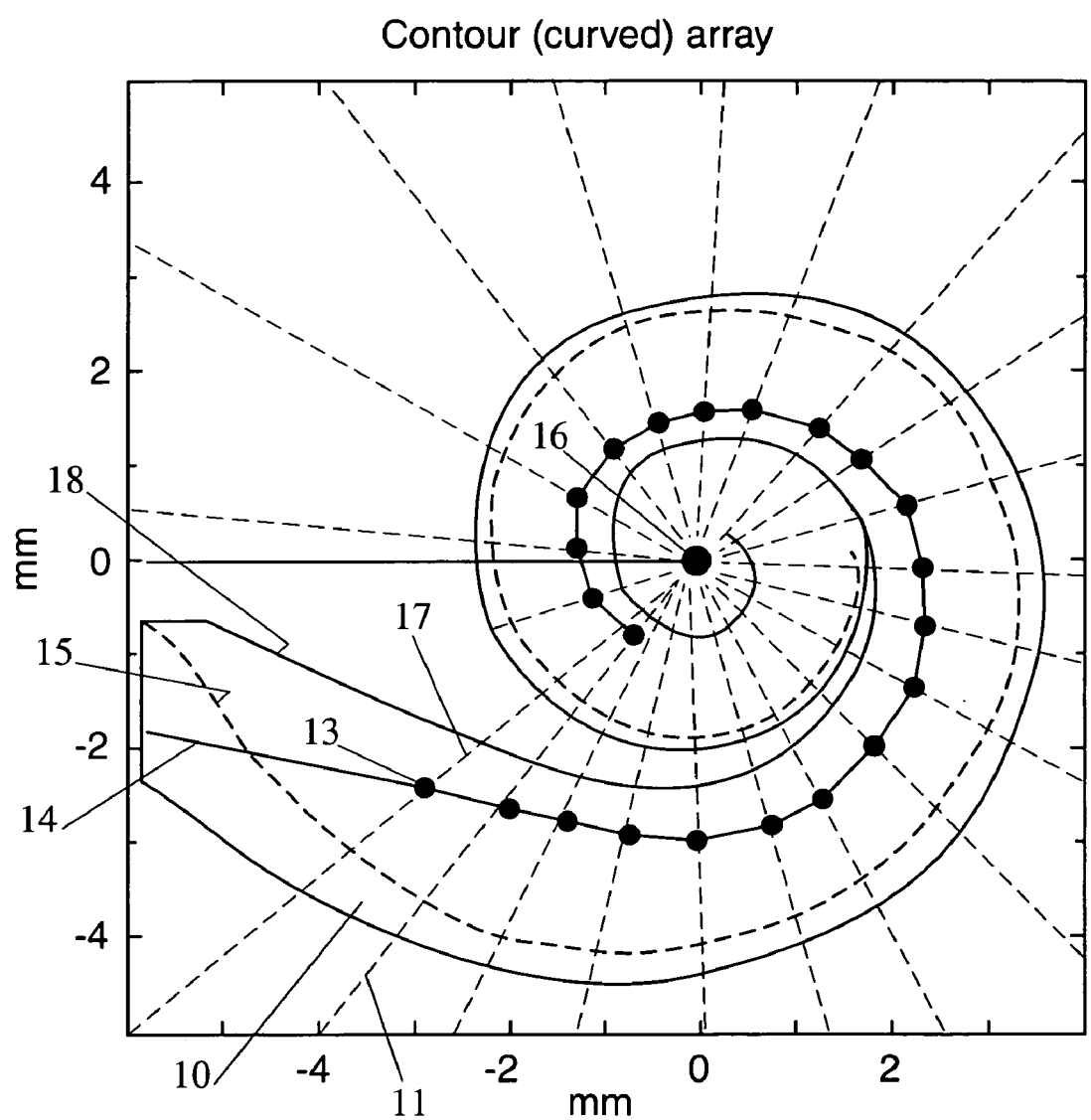
FIG. 2 is a schematic illustration of an electrode array with non-uniform spacing of electrodes.

As can be seen in FIG. 2, the receptors 17 on the inner wall 18, are spaced more and more closely together, as they approach the centre of the spiral of the cochlea. Thus, to maintain effective stimulation contact with receptors 17, electrodes 13 of the electrode array 14 are spaced with decreasing separation to each other the closer they approach the apical end of the electrode array 14.

Therefore, with an understanding of the physiology and geometry of the cochlea together with an understanding of the tonotopical nature of the cochlea, an electrode array can be designed to improve the fidelity of the reproduction of the audio spectrum in the percept of the cochlear implant recipient. This can be done by arranging the placement of the electrodes along the electrode array such that the spectral coverage of the electrodes are maximised to ensure optimum stimulation of the cochlea is achieved.

It will be appreciated that in the application of the present invention, the excitation by the electrodes is assumed to be substantially radial.

It may also be desired to take into account two further effects. The structures are considerably more complex than is apparent from the schematics. At the basal end of the scala tympani, the organ of Corti lies closer to the inner wall 18 and the spacing of the most basal electrodes could be reduced to take account of this. At the apical end, there is a greater angular offset between the organ of corti 15 and the underlying cell bodies, and again the spacing could be adjusted to account for this effect.

It will be appreciated by those skilled in the art that the present invention can be readily manufactured by existing techniques, and could be of any desired electrode geometry or cross-sectional shape. The present invention is concerned with the spacing of the electrodes, not their construction.

The invention claimed is:

1. An elongate electrode array for use in a cochlear implant, said electrode array comprising electrodes fixedly positioned longitudinally along said length of said electrode array such that, for any electrode and all of said electrodes of said electrode array, there is a space between adjacent electrodes, wherein said spaces between said adjacent electrodes change in a uniformly graduated manner along said length of said electrode array.

2. The electrode array of claim 1, wherein said electrode array is configured to be implanted in a recipient's cochlear, the cochlearing comprising a scala timpani having an inner wall and an outer wall, and a plurality of spaced auditory receptors positioned along said scala timpani, and wherein said spacing between said adjacent electrodes approximately corresponds with said spacing of auditory receptors on the inner wall of the scala timpani.

3. The electrode array of claim 1, wherein said electrode array is configured to be implanted in a recipient's cochlear, the cochlearing comprising a scala timpani having an inner wall and an outer wall, and a plurality of spaced auditory receptors positioned along said scala timpani, and wherein said electrode array is constructed to be positioned proximate to the inner wall of the scala timpani.

4. The electrode array of claim 1, wherein said electrode array has an apical end and a basal end, and wherein said spacing between said adjacent electrodes positioned toward said apical end of said electrode array are less than said spacing between said adjacent electrodes positioned toward said at a basal end of said electrode array.

5. The electrode array of claim 1, wherein said electrode array is adapted to deliver sound at specific frequency bands associated with speech recognition.

6. The electrode array of claim 1, wherein said electrode array is configured to be implanted in a recipient's cochlear, the cochlearing comprising a scala timpani having an inner wall and an outer wall, and a plurality of spaced auditory receptors positioned along said scala timpani, and wherein said uniform graduation of said spaces along said length of said electrode array so as to correspond with spacing of the receptors along the inner wall of the scala timpani.

7. The electrode array of claim 1, wherein said electrode array is configured to be implanted in a recipient's cochlear, the cochlearing comprising a scala timpani having an inner wall and an outer wall, and an organ of Corti with a plurality of spaced auditory receptors extending toward the inner wall of the scala timpani, and wherein said spaces between said adjacent electrodes change in a uniformly graduated manner along said length of said electrode array so as to correspond with spacing of the receptors along the inner wall of the scala timpani.

8. The electrode array of claim 1, wherein said electrode array is configured to be implanted in a recipient's cochlear, the cochlearing comprising a scala timpani having an inner wall and an outer wall, and an organ of Corti with a plurality of spaced auditory receptors extending toward the inner wall of the scala timpani, and wherein said spaces between said adjacent electrodes is determined by a plurality of radially-spaced intercept lines extending from the modiolar center point of the cochlear through a respective plurality of points spaced at equal increments along the organ of Corti.

9. An electrode array for use in a cochlear implant to be implanted in a recipient's cochlear, the cochlear comprising a scala timpani having an inner wall and an outer wall and spaced aural receptors disposed adjacent to the inner wall, the receptors being spaced closer to each other toward the modiolar center of the cochlear, said electrode array comprising electrodes selectively positioned longitudinally along said electrode array such that, for any electrode and all electrodes of said electrode array, spacing between consecutive electrodes are uniformly graduated from a distal end to a proximal end of the electrode array.

10. The electrode array of claim 9, wherein said spacing between said adjacent electrodes approximately corresponds with said spacing of auditory receptors on the inner wall of the scala timpani.

11. The electrode array of claim 9, wherein said electrode array is constructed to be positioned proximate to the inner wall of the scala timpani.

12. The electrode array of claim 9, wherein said spacing between said adjacent electrodes positioned toward said distal end of said electrode array are less than said spacing between said adjacent electrodes positioned toward said proximal end of said electrode array.

13. The electrode array of claim 9, wherein said electrode array uses specific frequency bands associated with speech recognition.

14. The electrode array of claim 9, wherein said electrode array is configured to be implanted in a recipient's cochlear, the cochlearing comprising a scala timpani having an inner wall and an outer wall, and a plurality of spaced auditory receptors positioned along said scala timpani, and wherein said spaces between said adjacent electrodes change in a uniformly graduated manner along said length of said electrode array so as to correspond with spacing of the receptors along the inner wall of the scala timpani.

15. The electrode array of claim 9, wherein said electrode array is configured to be implanted in a recipient's cochlear, the cochlearing comprising a scala timpani having an inner wall and an outer wall, and an organ of Corti with a plurality of spaced auditory receptors extending toward the inner wall of the scala timpani, and wherein said spaces between said adjacent electrodes change in a uniformly graduated manner along said length of said electrode array so as to correspond with spacing of the receptors along the inner wall of the scala timpani.

16. The electrode array of claim 9, wherein said electrode array is configured to be implanted in a recipient's cochlear, the cochlear comprising a scala timpani having an inner wall and an outer wall, and an organ of Corti with a plurality of spaced auditory receptors extending toward the inner wall of the scala timpani, and wherein said spaces between said adjacent electrodes is determined by a plurality of radially-spaced intercept lines extending from the modiolar center point of the cochlear through a respective plurality of points spaced at equal increments along the organ of Corti.

17. An auditory prosthesis comprising:
an elongate auditory electrode array comprising electrodes fixedly positioned longitudinally along said length of said electrode array such that, for any electrode and all of said electrodes, there is a space between adjacent electrodes, wherein said spaces between said adjacent electrodes change in a uniformly graduated manner along said length of said electrode array.

18. The auditory prosthesis of claim 17, wherein said electrode array is configured to be implanted in a recipient's cochlear, the cochlear comprising a scala timpani having an inner wall and an outer wall, and a plurality of spaced auditory receptors positioned along said scala timpani, and wherein said spacing between said adjacent electrodes approximately corresponds with said spacing of auditory receptors on the inner wall of the scala timpani.

19. The auditory prosthesis of claim 17, wherein said electrode array is configured to be implanted in a recipient's cochlear, the cochlear comprising a scala timpani having an inner wall and an outer wall, and a plurality of spaced auditory receptors positioned along said scala timpani, and wherein said electrode array is constructed to be positioned proximate to the inner wall of the scala timpani.

20. The auditory prosthesis of claim 17, wherein said electrode array has an apical end and a basal end, and wherein said spacing between said adjacent electrodes positioned toward said apical end of said electrode array are less than said spacing between said adjacent electrodes positioned toward said at a basal end of said electrode array.

21. The auditory prosthesis claim 17, wherein said electrode array uses specific frequency bands associated with speech recognition.

22. The auditory prosthesis of claim 17, wherein said electrode array is configured to be implanted in a recipient's cochlear, the cochlear comprising a scala timpani having an inner wall and an outer wall, and a plurality of spaced auditory receptors positioned along said scala timpani, and wherein said spaces between said adjacent electrodes change in a uniformly graduated manner along said length of said electrode array so as to correspond with spacing of the receptors along the inner wall of the scala tympani.

23. The auditory prosthesis of claim 17, wherein said electrode array is configured to be implanted in a recipient's cochlear, the cochlear comprising a scala timpani having an inner wall and an outer wall, and an organ of Corti with a plurality of spaced auditory receptors extending toward the inner wall of the scala timpani, and wherein said spaces between said adjacent electrodes change in a uniformly graduated manner along said length of said electrode array so as to correspond with spacing of the receptors along the inner wall of the scala tympani.

24. The auditory prosthesis of claim 17, wherein said electrode array is configured to be implanted in a recipient's cochlear, the cochlear comprising a scala timpani having an inner wall and an outer wall, and an organ of Corti with a plurality of spaced auditory receptors extending toward the inner wall of the scala timpani, and wherein said spaces between said adjacent electrodes is determined by a plurality of radially-spaced intercept lines extending from the modiolar center point of the cochlear through a respective plurality of points spaced at equal increments along the organ of Corti.

* * * * *